United States Patent [19]

Ayer

[11] 4,163,843
[45] Aug. 7, 1979

[54] 7A-HOMO-4-OXO-PGI₁ COMPOUNDS
[75] Inventor: Donald E. Ayer, Kalamazoo, Mich.
[73] Assignee: The Upjohn Company, Kalamazoo, Mich.
[21] Appl. No.: 904,188
[22] Filed: May 8, 1978

Related U.S. Application Data

[63] Continuation-in-part of Ser. No. 857,106, Dec. 5, 1977, Pat. No. 4,126,744.

[51] Int. Cl.² .......................................... C07D 307/93
[52] U.S. Cl. ................................... 542/426; 542/429; 542/430; 542/431; 260/244.4; 260/345.2; 260/326.36; 544/153; 544/376; 546/194; 546/196; 546/256; 546/269

[58] Field of Search ............. 260/345.2, 326.36, 244.4; 542/426, 429; 544/153, 376; 546/194, 196, 256, 269

[56] References Cited
PUBLICATIONS

Johnson et al., J.A.C.S. 99:12, Jun. 1977, pp. 4182–4185.

Primary Examiner—Natalie Trousof
Assistant Examiner—Bernard Dentz
Attorney, Agent, or Firm—Robert A. Armitage

[57] ABSTRACT

This invention relates to certain 7a-homo-4-oxo-PGI₁ compounds. These novel prostacyclin-type compounds are useful for pharmacological purposes.

43 Claims, No Drawings

7A-HOMO-4-OXO-PGI₁ COMPOUNDS

CROSS REFERENCE TO RELATED APPLICATIONS

This application is a continuation-in-part of Ser. No. 857,106, filed Dec. 5, 1977, now U.S. Pat. No. 4,126,744.

The present invention relates to 7a-homo-4-oxo-PGI₁ compounds whose preparation and use is described in Ser. No. 857,106, filed Dec. 5, 1977, now issued as U.S. Pat. No. 4,126,744.

The essential material constituting a disclosure of these 7a-homo-4-oxo-PGI₁ compounds is incorporated here by reference from U.S. Pat. No. 4,126,744.

I claim:
1. A prostacyclin analog of the formula

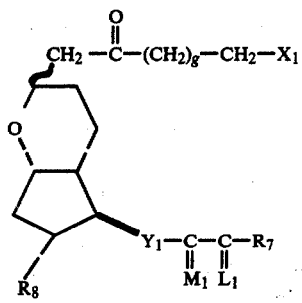

wherein ~ represents attachment of the side chain in the alpha or beta configuration or a mixture of alpha and beta configurations;
wherein g is the integer one, 2, or 3;
where $R_8$ is hydrogen, hydroxy, or hydroxymethyl;
wherein $Y_1$ is
  (1) trans —CH=Ch—,
  (2) cis —CH=CH—,
  (3) —CH₂CH₂—, or
  (4) —C≡C—,
wherein $M_1$ is

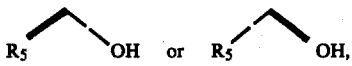

wherein $R_5$ is hydrogen or alkyl with one to 4 carbon atoms, inclusive,
wherein $L_1$ is

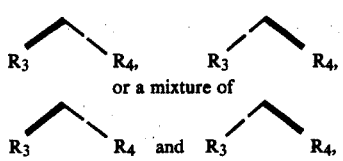

wherein $R_3$ and $R_4$ are hydrogen, methyl, or fluoro, being the same or different, with the proviso that one of $R_3$ and $R_4$ is fluoro only when the other is hydrogen or fluoro;
wherein $Z_1$ is
  (1) —COOR₁ wherein $R_1$ is hydrogen; alkyl of one to 12 carbon atoms, inclusive; cycloalkyl of 3 to 10 carbon atoms, inclusive; hydrocarbylaralkyl of 7 to 12 carbon atoms, inclusive; phenyl; phenyl substituted with one, two, or three chloro or alkyl of one to 3 carbon atoms; phenyl substituted in the para position by

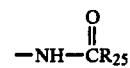
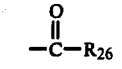
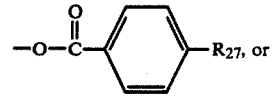

wherein $R_{25}$ is methyl, phenyl, acetamidophenyl, benzamidophenyl, or —NH₂; $R_{26}$ is methyl, phenyl, —NH₂, or methoxy; and $R_{27}$ is hydrogen or acetamido; inclusive, phenacyl, i.e.,

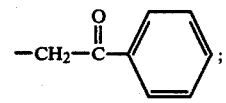

phenacyl substituted in the para position by chloro, bromo, phenyl, or benzamido; of a pharmacologically acceptable cation;
  (2) —CH₂OH; or
  (3) —COL₄, wherein $L_4$ is
    (a) amino of the formula —NR₂₁R₂₂; wherein $R_{21}$ and $R_{22}$ are hydrogen; alkyl of one to 12 carbon atoms, inclusive; cycloalkyl of 3 to 10 carbon atoms, inclusive; aralkyl of 7 to 12 carbon atoms, inclusive; phenyl; phenyl substituted with one, 2, or 3 chloro, alkyl of one to 3 carbon atoms, inclusive, hydroxy, carboxy, alkoxycarbonyl of one to 4 carbon atoms, inclusive, or nitro; carboxyalkyl of one to 4 carbon atoms, inclusive; carbamoylalkyl of one to 4 carbon atoms, inclusive; cyanoalkyl of one to 4 carbon atoms, inclusive; acetylalkyl of one to 4 carbon atoms, inclusive; benzoylalkyl of one to 4 carbon atoms, inclusive; benzoylalkyl substituted by one, 2, or 3 chloro, alkyl of one to 3 carbon atoms, inclusive, hydroxy, alkoxy of one to 3 carbon atoms, inclusive, carboxy, alkoxycarbonyl of one to 4 carbon atoms, inclusive, or nitro; pyridyl; pyridyl substituted by one, 2, or 3 chloro, alkyl of one to 3 carbon atoms, inclusive, or alkoxy of one to 3 carbon atoms; inclusive; pyridylalkyl of one to 4 carbon atoms, inclusive; pyridylalkyl substituted by one, 2, or 3 chloro, alkyl of one to 3 carbon atoms, inclusive, hydroxy, or alkoxy of one to 3 carbon atoms, inclusive; hydroxyalkyl of one to 4 carbon atoms, inclusive; dihydroxyalkyl of one to 4 carbon atoms, and trihydroxyalkyl of one to 4 carbon atoms; with the further proviso that not more than one of $R_{21}$ and $R_{22}$ is other than hydrogen or alkyl;
    (b) cycloamino selected from the group consisting of

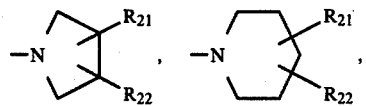

-continued

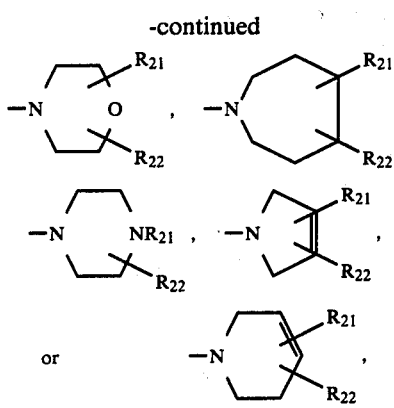

wherein $R_{21}$ and $R_{22}$ are as defined above;
(c) carbonylamino of the formula —$NR_{23}COR_{21}$, wherein $R_{23}$ is hydrogen or alkyl of one to 4 carbon atoms and $R_{21}$ is as defined above;
(d) sulfonylamino of the formula —$NR_{23}SO_2R_{21}$, wherein $R_{21}$ and $R_{23}$ are as defined above; or
(e) hydrazino of the formula —$NR_{23}R_{24}$, wherein $R_{23}$ is as defined above and $R_{24}$ is amino of the formula —$NR_{21}R_{22}$, as defined above, or cycloamino, as defined above; and wherein $R_7$ is
(1) —$(CH_2)_m$—$CH_3$,

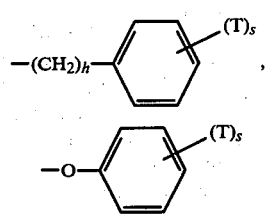

wherein m is the integer one to 5, inclusive, h is the integer zero to 3, inclusive; s is the integer zero, one, 2, or 3, and T is chloro, fluoro, trifluoromethyl, alkyl of one to 3 carbon atoms, inclusive, or alkoxy of one to 3 carbon atoms, inclusive, with the proviso that not more than two T's are other than alkyl.

2. A prostacyclin analog according to claim 1, wherein $R_8$ is hydroxymethyl.

3. 7a-Homo-11-deoxy-11α-hydroxymethyl-4-oxo-6α- or 6β-$PGI_1$, a prostacyclin analog according to claim 2.

4. A prostacyclin analog according to claim 1, wherein $R_8$ is hydrogen.

5. 7a-Homo-11-deoxy-4-oxo-6α- or 6β-$PGI_1$, a prostacyclin analog according to claim 4.

6. A prostacyclin analog according to claim 1, wherein $R_8$ is hydroxy.

7. A prostacyclin analog according to claim 6, wherein $Y_1$ is cis —CH=CH—, —C≡C—, or —$CH_2CH_2$—.

8. 7a-Homo-cis-13-4-oxo-$PGI_1$, a prostacyclin analog according to claim 7.

9. 7a-Homo-13,14-Didehydro-4-oxo-6α- or 6β-$PGI_1$, a prostacyclin analog according to claim 7.

10. 7a-Homo-13,14-Dihydro-4-oxo-6α- or 6β-$PGI_1$, a prostacyclin analog according to claim 7.

11. A prostacyclin analog according to claim 6, wherein $Y_1$ is trans —CH=CH—,

12. A prostacyclin analog according to claim 11, wherein the C-6 side chain is a mixture of alpha and beta isomers.

13. 7a-Homo-(6RS)-4-oxo-$PGI_1$, a prostacyclin analog according to claim 1.

14. A prostacyclin analog according to claim 11, wherein the C-6 side chain is in the alpha configuration.

15. 7a-Homo-4-oxo-6α-$PGI_1$, a prostacyclin analog according to claim 14.

16. A prostacyclin analog according to claim 11, wherein the C-6 side chain is in the beta configuration.

17. A prostacyclin analog according to claim 16, wherein g is two.

18. 2a,7a-Dihomo-4-oxo-6β-$PGI_1$, a prostacyclin analog according to claim 17.

19. A prostacyclin analog according to claim 16, wherein g is one or 3.

20. A prostacyclin analog according to claim 19, wherein g is one.

21. A prostacyclin analog according to claim 20, wherein $R_7$ is $$-(CH_2)_h-\underset{}{\underset{}{\bigcirc}}-(T)_s.$$

22. 7a-Homo-17-phenyl-18,19,20-trinor-4-oxo-6β-$PGI_1$, a prostacyclin analog according to claim 21.

23. A prostacyclin analog according to claim 20, wherein $R_7$ is $$-O-\underset{}{\underset{}{\bigcirc}}-(T)_s.$$

24. 7a-Homo-16-phenoxy-17,18,19,20-tetranor-4-oxo-6β-$PGI_1$, a prostacyclin analog according to claim 23.

25. A prostacyclin analog according to claim 20, wherein $R_7$ is —$(CH_2)_m$—$CH_3$—.

26. A prostacyclin analog according to claim 25, wherein m is 3.

27. A prostacyclin analog according to claim 26, wherein $X_1$ is —$COL_4$.

28. 7a-Homo-4-oxo-6β-$PGI_1$, amide, a prostacyclin analog according to claim 27.

29. A prostacyclin analog according to claim 27, wherein $X_1$ is —$CH_2OH$.

30. 7a-Homo-2-decarboxy-2-hydroxymethyl-4-oxo-6β-$PGI_1$, a prostacyclin analog according to claim 29.

31. A prostacyclin analog according to claim 26, wherein $X_1$ is —$COOR_1$.

32. A prostacyclin analog according to claim 31, wherein $R_5$ is methyl.

33. 7a-Homo-15-methyl-4-oxo-6β-$PGI_1$, a prostacyclin analog according to claim 32.

34. A prostacyclin analog according to claim 31, wherein $R_5$ is hydrogen.

35. A prostacyclin analog according to claim 34, wherein at least one of $R_3$ and $R_4$ is fluoro.

36. 7a-Homo-16,16-difluoro-4-oxo-6β-$PGI_1$, a prostacyclin analog according to claim 35.

37. A prostacyclin analog according to claim 34, wherein at least one of $R_3$ and $R_4$ is methyl.

38. 7a-Homo-16,16-dimethyl-4-oxo-6β-$PGI_1$, a prostacyclin analog according to claim 37.

39. A prostacyclin analog according to claim 34, wherein $R_3$ and $R_4$ are both hydrogen.

40. 7a-Homo-4-oxo-6β-PGI$_1$, methyl ester, a prostacyclin analog according to claim 39.

41. 7a-Homo-4-oxo-6β-PGI$_1$, tris(hydroxymethyl)amino methane salt, a prostacyclin analog according to claim 39.

42. 7a-Homo-4-oxo-6β-PGI$_1$, adamantanamine salt, a prostacyclin analog according to claim 39.

43. 7a-Homo-4-oxo-6β-PGI$_1$, a prostacyclin analog according to claim 39.

* * * * *

UNITED STATES PATENT OFFICE
CERTIFICATE OF CORRECTION

Patent No. 4,163,843     Dated 7 August 1979

Inventor(s) Donald E. Ayer

It is certified that error appears in the above-identified patent and that said Letters Patent are hereby corrected as shown below:

Column 1, line 38, "trans-CH=Ch-," should read -- trans-CH=CH-, --;

Column 4, line 5, "according to claim 1." should read -- according to claim 12. --.

*Signed and Sealed this*

*Twenty-eighth* Day of *October 1980*

[SEAL]

*Attest:*

SIDNEY A. DIAMOND

*Attesting Officer*     *Commissioner of Patents and Trademarks*